US006335035B1

(12) United States Patent
Drizen et al.

(10) Patent No.: US 6,335,035 B1
(45) Date of Patent: \*Jan. 1, 2002

(54) SUSTAINED RELEASE DELIVERY SYSTEM

(75) Inventors: Alan Drizen; Peter Rothbart, both of Ontario (CA); Gary M. Nath, Bethesda, MD (US)

(73) Assignee: L.A.M. Pharmaceutical Corporation, North York (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/514,163

(22) Filed: Feb. 28, 2000

Related U.S. Application Data

(62) Division of application No. 09/049,653, filed on Jan. 8, 1998, now Pat. No. 6,063,405, which is a continuation of application No. 08/588,272, filed on Jan. 18, 1996, now abandoned, which is a continuation of application No. 08/536,750, filed on Sep. 29, 1995, now abandoned.

(51) Int. Cl.$^7$ ................................................. A61K 9/14
(52) U.S. Cl. ....................... 424/488; 424/484; 424/486; 424/485
(58) Field of Search ................................ 424/484, 486, 424/488, 78.08, 485; 514/54, 568, 777, 781, 825, 886, 887, 944; 536/53; 548/500; 549/554; 560/47; 562/426, 492; 564/141, 144

(56) References Cited

U.S. PATENT DOCUMENTS

| | | | |
|---|---|---|---|
| 4,127,118 A | 11/1978 | Latorre | |
| 4,291,015 A | 9/1981 | Keith et al. | |
| 4,322,433 A | 3/1982 | Leslie et al. | |
| 4,636,524 A | 1/1987 | Balazs et al. | |
| 4,801,587 A | 1/1989 | Voss et al. | |
| 4,829,991 A | 5/1989 | Boeck | |
| 5,143,724 A | 9/1992 | Leshchiner et al. | |
| 5,219,885 A | 6/1993 | Frolich et al. | |
| 5,356,629 A | 10/1994 | Sander et al. | |
| 5,464,868 A | 11/1995 | Frolich et al. | |
| 5,488,059 A | 1/1996 | Buhl | |
| 5,646,181 A | 7/1997 | Fung et al. | |
| 5,681,850 A | 10/1997 | Frolich et al. | |
| 5,686,425 A | 11/1997 | Lee | |
| 5,708,031 A | 1/1998 | Scott | |
| 5,709,883 A | * 1/1998 | Drizen et al. | 424/488 |
| 5,716,631 A | * 2/1998 | Drizen et al. | 424/422 |
| 5,807,581 A | * 9/1998 | Rosenblatt et al. | 424/484 |
| 5,851,229 A | * 12/1998 | Lentz et al. | 623/1 |
| 5,866,113 A | * 2/1999 | Hendriks et al. | 424/78.17 |
| 5,866,619 A | * 2/1999 | Sintov et al. | 514/777 |
| 6,007,833 A | * 12/1999 | Chudzik et al. | 424/425 |

FOREIGN PATENT DOCUMENTS

WO    92/03141    3/1992

OTHER PUBLICATIONS

Billmeyer. Textbook of Polymer Science. Interscience Publishers. New York, N.Y. 1962, see pp. 62–104.

Kirk–Othmer. Encyclopedia of Chemical Technology, $2^{nd}$ Ed. vol. 16, 1968, see pp. 242–253.

Nakajima, "Fractionation of Linear Polyethylene with Gel Permeation Chromatography", Advances in Chemistry Series 125, Published by American Chemical Society, pp. 89–107 (1973).

* cited by examiner

*Primary Examiner*—Diana Dudash
*Assistant Examiner*—Mina Haghighatian
(74) *Attorney, Agent, or Firm*—Nath & Associates PLLC; Gary M. Nath

(57) ABSTRACT

Sustained release compositions comprising a drug dispersed within a polymer matrix, methods of producing the same and treatments with the complex.

11 Claims, No Drawings

SUSTAINED RELEASE DELIVERY SYSTEM

This application is a divisional application of U.S. patent application Ser. No. 09/049,653, filed Jan. 8, 1998, now U.S. Pat. No. 6,063,405, which is a continuation of U.S. patent application Ser. No. 08/588,272, filed Jan. 18, 1996, abandoned, which is a continuation of U.S. patent application Ser. No. 08/536,750, filed Sep. 29, 1995, now abandoned, the entire contents of all three being hereby incorporated in their entirety.

BACKGROUND OF INVENTION

1. Field of the Invention

This invention relates to the preparation of a sustained release delivery system, and more particularly to a system using a polymer matrix containing a drug. The system is designed to administer effective levels of drugs over a sustained period of time when administered intramuscularly, epidurally or subcutaneously for the treatment of various disease states conditions. A particularly advantageous use of the system is the administration of a local anesthetic along the sheath of a nerve or muscle tissue to alleviate or ameliorate the effects of pain.

2. Description of the Prior Art

Medications have been formulated to enable the administration of drugs to occur over a wide variety of paths, including instantaneous delivery by use of injectables, and sustained, controlled and extended release delivery by use of tablets, capsules, and particulate forms which enable release of the drug to be controlled by various means, such as by resistance of the structure's coating or composition against diffusion of the drug therethrough. These systems have all found wide applications for the delivery of drugs.

None of the known drug delivery systems, however, are able to administer effective therapeutic amounts of a drug for sustained periods of time, that is, longer than 24 to 48 hours. Actually, most delivery systems maintain effective dosages for from several hours to daily doses before requiring readministration. Such systems have not been found to be effective for the long term administration of drugs that require repetitive and continued use, except of course for selected patch treatments. Drugs that have been repeatedly administered for long term treatments include but are not limited to anesthetics for treating pain, steroids and hormone administration for maintenance, modification or alteration of body chemistry, metabolism and hormone balance and regulation, vitamin and mineral supplementation, and so forth. A delivery system is therefore needed which would permit the administration of therapeutically effective amounts of drugs to enable a continued and sustained release for at least 24 hours to several days.

SUMMARY OF THE INVENTION

The present invention relates to the formation of a long-acting drug composition for use in treating acute, or chronic conditions. More particularly, this invention relates to a sterilized, purified, solubilized or suspended drug composition, which comprises: a drug dispersed within a polymer matrix solubilized or suspended in a polymer matrix, with or without the presence of a preservative. The polymer matrix is composed of a highly negative charged polymer material selected from the group consisting of polysulfated glucosoglycans, glycosaminoglycans, mucopolysaccharides and mixtures thereof, and a nonionic polymer selected from the group consisting of carboxymethylcellulose sodium, hydroxyethyl cellulose, hydroxypropyl cellulose, and mixtures thereof.

Another embodiment of this invention involves a method for the treatment of a condition in animals, which comprises injecting therapeutically effective dosages of a suspension or solution of a sterilized, purified, solubilized or suspended composition comprising a drug dispersed within a polymer matrix which is solubilized or suspended in a liquid medium. Preferably, one of the polymer materials has a mean average molecular weight below about 800,000, and the other polymer is a nonionic cellulose derivative.

DETAILED DESCRIPTION OF THE INVENTION

The present invention relates to the formation of a delivery system for administering a drug for a sustained period, and particularly to a polymer matrix useful for its treatment of acute, or chronic intractable pain and to the use therefor. The process involves the production and use of specialized compounds manufactured by using polymers of molecular weights below about 800,000 in a unique process for the creation of specially modified molecules to treat a variety of conditions. Specifically, the invention addresses a process for manufacturing a polymer matrix suspended or solubilized in water with various drugs. The polymers must be sterilizable and acceptable for animal, and human use. In this way, a suitable polymer system is formed as a matrix which is able to disperse a much lower molecular weight drug to form a solution or suspension of the active for subsequent use.

It has been found in conventional drug treatments that once a therapeutic dosage is used, the beneficial effect of such dosage routine wears off within several hours of its initial application, thus requiring repetitive treatment. This mechanism is common in all animal systems and involves biochemical pathways that have not yet been fully discovered or identified. One possibility for this action would involve the animals own immunoglobin system which may be responsible for identifying the presence of the chemical entity and systematically destroying it. Another may be the inherent instability of the chemical entity after its administration into the animal.

It has been unexpectedly discovered that an effective therapeutic level of a drug may be administered once over at least a 24 hour to several day interval when the drug is suspended or entrapped in a specially designed polymer matrix containing almost equal molar ratios of a negatively charged polymer and a nonionic polymer suspended or dissolved in water.

This system is believed to form a matrix which microencapsulates, suspends and/or entraps the active drug entity such that when it is administered it is slowly released into the systemic circulatory system or muscular tissue providing a sustained and prolonged drug release rate.

The molar ratio of the polymers present in the matrix is critical in this invention. It has been found that molar ratios of the negatively charged polymer to the nonionic polymer must be from 1:0.5 to 2 and preferably from 1:0.8 to 1.5 and most preferably from 1:1 to 1.2. At ratios either higher or lower than these levels the resulting systems tend to sheer when being prepared and form unacceptable air pockets and bubbles. Furthermore, the solutions tend to separate and form distinct polymer layers.

At least one of the polymers used to form the matrix of this invention must be sufficiently negatively charged to aid in the dispersion, encapsulation or solubilization of the drug. Particularly preferred polymers have mean average molecular weights below about 800,000 and preferably molecular weights between about 500,000 to 800,000 have been found acceptable to form useable polymer matrixes. Polymers with mean average molecular weights between about 700,000 and 775,000 are most preferred. Polymers having molecular weights above about 800,000 form solid gels in solution and are unable to serve in an injectable system. Furthermore, the polymers must be sterilizable and be stable during sterilization so that the polymer does not lose molecular weight once formulated into the final injectable form Exemplary, non-limiting examples of compounds that may be used as a source of this molecular weight polymer include polysulfated glucosoglycans, glucosaminoglycans, and mucopolysaccharides, derivatives thereof and mixtures thereof. Particularly preferred mucopcolysaccharides are chondroitin sulfate and hyaluronic acid salts with sodium hyaluronate being most preferred.

Hyaluronic acid (HA) occurs naturally in joint synovial fluid, where it plays a lubricating role, and may have biological activity as well. HA is a mucopolysaccharide, and may alternatively be referred to as a glycosaminoglycan. The repeating unit of the hyaluronic acid molecule is a disaccharide consisting of D-glucuronic acid and N-acetyl-D-glucosamine. Because hyaluronic acid possesses a negative charge at neutral pH, it is soluble in water, where it forms highly viscous solutions. The D-glucuronic acid unit and N-acetyl-D-glucosamine unit are bonded through a glycosidic, beta (1–3) linkage, while each disaccharide unit is bonded to the next disaccharide unit through a beta (1–5) linkage. The (beta 1–4) linkages may be broken through hydrolysis with the enzyme hyaluronidase.

A variety of substances, commonly referred to as hyaluronic acid, have been isolated by numerous methods from various tissue sources including umbilical cords, skin, vitreous humour, synovial fluid, tumors, haemolytic streptocci pigskin, rooster combs, and the walls of veins and arteries. It is also being synthesized artificially and by recombinant technology.

Conventional methods for obtaining hyaluronic acid results with a product having differing properties and a wide range of viscosities. U.S. Pat. No. 2,585,546 to Hadian, discloses an example of a method for obtaining hyaluronic acid and which involves extracting acetone-washed umbilical cords with a dilute salt solution, acidifying the resulting extract, removing the clot so formed, precipitating some hyaluronic acid with protein from the acidified extract with ammonium sulfate, agitating the liquid with pyridine, precipitating another fraction highly contaminated with protein, followed by more ammonium sulfate which forces some pyridine out of solution along with the high viscosity hyaluronic acid. The hyaluronic acid collects at the interface between the two liquid phases and may be separated by filtration, centrifugation or other usual procedure. A modification of this process involves the fractionation of the acidic salt extract from umbilical cords with alcohol and ammonium sulfate. Alcohol is added to the acidic salt extract, and the resulting precipitate is removed. Solid ammonium sulfate is added to the liquid until saturation and the solution forms two phases with a precipitate of hyaluronic acid at the interface.

U.S. Pat. No. 4,517,296 to Bracke et al, is directed to the preparation of hyaluronic acid in high yield from streptococcus bacteria by fermenting the bacteria under anaerobic conditions in a $CO_2$ enriched growth medium, separating the bacteria from the resulting broth and isolating the hyaluronic acid from the remaining constituents of the broth. Separation of the microorganisms from the hyaluronic acid is facilitated by killing the bacteria with trichloroacetic acid. After removal of the bacteria cells and concentration of the higher molecular weight fermentation products, the hyaluronic acid is isolated and purified by precipitation, resuspension and reprecipitation.

One particular fraction of hyaluronic acid (HA) that exhibits excellent matrix formation according to the present invention is hyaluronate sodium having a molecular weight of between 650,000–800,000, preferably 700,000–775,000 with a high degree of purity, 95–100% free, and preferably at least 98% pure, from contamination of related mucopolysaccharides. Furthermore, this hyaluronic acid has a sulphated ash content of less than 15% and a protein content of less than 5%. Examples of usable base salts include those safe for animal and human use, such as sodium, potassium, calcium, and magnesium salts or the like.

In contrast to HA, chondroitins are mucopolysaccharides comprising repeating units of D-glucuronic acid and N-acetyl-D-galactosamine. Chondroitin sulphates are important components of cartilage and bone and are excellent for preparing the polymer matrix herein.

The negative charged polymers are generally present in the system in amounts which enable a solution or solid gel to be formed. Generally, solutions are formed using amounts of about 0.1 to 2.0% by weight with amounts of about 1 to about 1.5% by weight being preferred for use as an injectable. Topical gel forms may be prepared with amounts of about 2.0% to about 3.0% by weight. A particularly preferred sodium HA concentration as an injectable is 1.3% by weight.

In addition to the negatively charged polymers, the polymer matrix must contain a nonionic polymer which aids in retarding the rate of absorption of the active drug and delays or slows down an animals natural absorption of the negatively charged polymer. Without the presence of this component, the drug would be rapidly absorbed, and sustained action of the active could not be achieved. Particularly preferred nonionic polymers are cellulose derivatives and particularly those selected from the group consisting of carboxymethylcellulose sodium, hydroxyethyl cellulose, hydroxypropyl cellulose and mixtures thereof. These particular polymers have been found to possess exceptional ability to form sustained release matrix formulations when used in combination with a negatively charged polymer. Such polymers are generally employed in amounts of about 0.1% to about 1.0% and preferably about 0.5 to about 1.0%. Amounts above about 1.0% result in the formation of a solid gel product when used with the negatively charged polymer. Amounts below about 0.1% have not been found suitable to prepare a storage stable solution or form a product that has sustained drug release.

A wide variety of medicaments which are administered may be used in the delivery system according to this invention. These include drugs from all major categories, and without limitation, for example, anesthetics including those used in caudal, epidural, inhalation, injectable, retrobulbar, and spinal applications, such as bupivacaine and lidocaine; analgesics, such as acetaminophen, ibuprofen, fluriprofen, ketoprofen, voltaren (U.S. Pat. No. 3,652,762), phenacetin and salicylamide; anti-inflammatories selected from the group consisting of naproxen and indomethacin; antihistamines, such as chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; antitussive selected from the group consisting of dextromethorphan hydrobromide and guaifenesin; expectorants such as guaifenesin; decongestants, such as phenylephrine hydrochloride, phenylpropanolamine hydrochloride, pseudoephedrine hydrochloride, ephedrine; antibiotics including amebicides, broad and medium spectrum, fungal medications, monobactams and viral agents and specifically including such as erythromycin, penicillin and cephalosporins and their derivatives; bronchodilators such as theophylline, albuterol and terbutaline; cardiovascular preparations such as diltiazem, propranolol, nifedepine and clonidine including alpha adrenoceptro agonist, alpha receptor blocking agent, alpha and beta receptor blocking agent, antiotensin converting enzyme inhibitors, beta blocking agents, calcium channel blocker, and cardiac glycosides; central nervous system drugs such as thioridazine, diazepam, meclizine, ergoloid mesylates, chlorpromazine, carbidopa and levodopa; metal salts such as potassium chloride and lithium carbonate; minerals selected from the group consisting of iron, chromium, molybdenum and potassium; immunomodulators; immunosuppressives; thyroid preparations such as synthetic thyroid hormone, and thyroxine sodium; steroids and hormones including ACTH, anabolics, androgen and estrogen combinations, androgens, corticoids and analgesics, estrogens, glucocorticoid, gonadotropin, gonadotropin releasing, human growth hormone, hypocalcemic, menotropins, parathyroid, progesterone, progestogen, progestogen and estrogen combinations, somatostatin-like compounds, urofollitropin, vasopressin, and others; and vitamins selected from water-soluble vitamins such as B complex, vitamin C, vitamin B12 and folic acid and veterinary formulations.

Particularly preferred dosage forms involve use of bupivacaine, lidocaine, vitamin B12, methyl prednisolone and adenosine-5-monophosphate sodium.

The solutions or suspensions of the present invention may be prepared in a variety of ways. For example, the polymers may be dissolved in water and purified either separately or jointly and then the active drug added to the system.

A particularly preferred procedure involves separately dissolving the nonionic polymer in water and centrifuging the material to form a solution and remove impurities. This may be conveniently done at rotation speeds of 2000 rpm for times of about 30 minutes to about two hours.

In contrast, the charged polymer may be blended and stirred in water until it is dissolved. This process must be done while avoiding the formation of bubbles and while freeing the polymer of its electrostatic activity. Furthermore, the molecular weight of the polymer must not be significantly changed during processing and as such mild process conditions are required. Processing conditions of 400–600 rpm for durations of 16–24 hours have been found acceptable to produce stable solutions or gels of the charged polymer.

Once the solutions are prepared, they may be mixed together and blended at moderate speeds to produce a homogenous solution (400–600 rpm for several hours).

The drug may then be added to the homogenous solution or separately dissolved or disbursed in water. Emulsifiers, suspending agents and preservatives may then be added to this system. Once all the components are blended together, 400–600 rpm for 1 to 4 hours, the system is filled into tubes and sterilized. The resulting system is a clear solution which is storage stable for several years.

When gels are prepared, the resulting system is also a clear gel or opaque which can be filled into tubes or containers and stored for future use. The formulations may be used topically and also contain conventional pharmaceutically acceptable excipients well known to those skilled in the art, such as surfactants, suspending agents, emulsifiers osmotic enhancers, extenders and dilutants, pH modifiers as well as fragrances, colors, flavors and other additives.

The dosage system can be formed with or without the use of preservatives. A significant advantage of the form of the present system relates to its ability to diffuse through tissue when injected intramuscularily, epidurally or subcutaneously as well as when applied topically. Additionally, it results in immediate and continued drugs release for long periods of time spanning at least 24 hours to even days.

The dosage form of this invention, in solution or suspension form, may be used by injection intramuscularly, epidurally or subcutaneously. Dosages may vary from patient to patient depending on the type and severity of the condition being treated and drug being administered.

The formulations of this invention may be used to treat a variety of animal conditions and physical states. These systems have particular application to pain management, namely the treatment and alleviation of pain associated with any disease condition or physical state.

Without being limited to the specific pain being treated, the preparations of this invention may treat the following nonlimiting locations or sources of pain: abdominal, such as in appendicitis, dysmenorrhea, musculoskeletal, pelvic, peptic ulcer, psychogenic, and urologic; acute; arm; backache; cancer; cardiac (myocardial ischemia); chest; dental; ear; esophageal; eye; face; head; and neck; in fibromyalgia; foot; and leg; heel; ischemic pain such as in myocardial, peripheral arterial, low back, in mitral valve prolapse, in myocardial infarction, myofascial pain syndrome (fibromyalgia, fibromyositis), neck, neuropathic, neurotransmitter abnormality, nociceptive, and nocturnal pain; pelvic; pericardial; in peripheral arterial disease; phantom limb; pleuritic; polyneuropathy; postmastectomy syndrome; postoperative; psychogenic; in pulmonary embolism; in renal disease, such as colic; root avulsions; shoulder; stump; thalamic; in toes; and toothache.

Besides chronic and intractable pain where injections of the complex may be required, the present complexes may be used to aid in post surgical pain treatments. With regard to uses after surgery, the complex may be used following abdominal, cervical, thoracic or cardiac surgery, whereby multiple layers of tissue, as being sewed back together are treated with the system. Such treatments aid in a patient's recovery by not only avoiding addictive drug use such as a morphine drip, but result in the immediate and long term relief of pain to enable rapid rehabilitation.

When used epidurally, the formulations of this invention have been round to alleviate pain without the loss of motor or sensory functions. This result is completely unexpected and not known with prior epidural nerve blocks. In this way, patients who are treated epidurally experience a remission or loss of the cain during the time period being treated yet maintain substantially all motor and sensory skills and functions.

It has also been unexpectedly found that when the system is administered in a repetitive manner, once the effects of the active drug are reduced in intensity or effectiveness, such repeat treatments result in a synergistic effect by enhancing the initial term of relief to a period which exceeds the initial time of relief. This is also experienced on subsequent treatments. In this ways the present formulations are able to extend relief or treatment from normally several hours to at least 24 hours to several days of relief. The use of repeat injections thus enhances drug release which significantly reduces drug dependence. It also results in the relief of continued tissue damage and may even assist in tissue repair.

Regardless of the route of administration elected, the formulations of the present invention are formulated into pharmaceutically acceptable dosage forms by conventional methods known in the pharmaceutical art. In general, a preferred method of administration is, however, by injectable or topical dosage forms. They may also be introduced epidurally and parenterally, (e.g., subcutaneously, or intramuscularly), using forms known to the pharmaceutical art as well as topically using the gelled form.

As discussed above, an effective but nontoxic amount of the system is employed in treatment. The dosage regimen for administering drugs or treating various conditions, such as pain as described above, is selected in accordance with a variety of factors including the type, age, weight, sex, and medical condition of the subject, he severity of the pain, the route of administration and the particular complex or combination or drugs employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired. Generally, amounts of drug may vary from 9.0001% to about 50% by weight of the system.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLE 1

This example demonstrates the formation of an anaesthetic preparation which produces long-acting anaesthesia either when injected epidurally, or intramuscularly.

| MATERIALS | |
|---|---|
| Bupivacaine | 0.65% |
| Hydraxyethyl cellulase (HEC) | 1.1% |
| Hyaluranate Sodium (HA) | 1.0% |
| Sterile Water | Q.S. |
| Batch Size | 1000 ml |

Into a sterilized glass vessel is added 500 ml of the sterile water which is stirred at 400–600 rpms. Slowly add 10 grams of HA having a molecular weight or around 700,000 to 775,000 and a purity described previously.

Allow to stir for 10–20 hours until all the HA Polymer has dissolved into the water and a crystal clear viscous solution has formed.

Prepare a 1.1% solution of HEC by adding 11 grams of the solid material, under aseptic conditions to 275 ml of sterile water. Allow to dissolve for 1 to 2 hours while stirring. Add the HEC solution to the HA solution and mix for 2 to 4 hours at 400–600 rpms until a homogenous solution is produced.

Dissolve 6.5 grams of bupivacaine (bupivacaine) in 225 ml of the sterile water and allow to mix for 1–2 hours at 200–400 rpms. Slowly add the bupivacaine solution to the HA/HEC homogenous mixture and mix for 2–4 hours at 400–600 rpms.

The resulting product is a clear solution which should be free of air bubbles.

Using aseptic techniques, the solution is then filled into suitable vials or ampules for use and stored.

EXAMPLE 2

The procedure of Example 1 was repeated except that the bupivacaine was replaced with 2% lidocane. The resulting product was a clear solution free of air bubbles.

EXAMPLE 3

The procedure of Example 1 was repeated except that the bupivacaine was replaced with 10% adenosine-5-monophosphate sodium. The resulting product was a clear solution free of air bubbles.

EXAMPLE 4

The procedure of Example 1 was repeated except that the bupivacaine was replaced with 20 to 80 mg/ml methyl prednesolone. The resulting product was a homogenous and misicable suspension.

EXAMPLE 5

The procedure of Example 1 was repeated except that the bupivacaine was replaced with various vitamins, namely 10 milligrams $B_1$, or 15 micrograms folio acid, 1000 micrograms Vitamin $B_{12}$, or 2 milligrams each of Vitamin $B_2$ and $B_6$. The resulting product was a clear solution of free air bubbles.

EXAMPLE 6

This example demonstrates the use in vivo of the Example 1 preparation with various patients suffering from chronic pain.

Run A

A 51-year old man has complained of pain in the right temple(this had been present for 15 years), pain in the neck; and generalized headaches.

In 1979, Mr. A was struck in the right temporoparietal area by a heavy machine while at work. Afterwards he developed severe pain in the right temporoparietal area. This gradually spread to involve the whole right side of his head. The pains became more and more frequent until they became constant. In addition he has in the last few years developed ongoing neck pain and generalized headaches.

Physical Examination

Physical examination has revealed tenderness in the right temporoparietal area as well as in the right supraorbital area and also in the right occipital area. he also has tenderness of the right facet joints and less so on the left. Investigations have included:

1. CT scans of the brain
2. X-rays of the head
3. X-rays of the neck
4. Facet diagnostic blocks of the cervical spin
5. CT myelogram of the cervical spin

Patient A's Diagnosis is as Follows

1. Damage of the peripheral nerves around the periosteum in the right temporoparietal area. (Site of injury headache)

2. Facet joint disease of the cervical spin
3. Recent cervical disc herniation

Patient A has Undergone the Following Treatments that Provided Up to 1 Day of Relief 1. Injections with local anesthetic and occasionally with steroids of the right supraorbital and temporoparietal area
2. Occipital blocks
3. Paravertebral blocks of the cervical facet joints In general, the tempoproparietal blocks have provided about one day of relief.

Treatment with the Example 1 Formulation

Injections were carried out in the right temporal parietal area using about 8 cc of the long-acting bupivacaine formulation.

In addition one injection was made into the paracervical muscle.

Result

The patient obtained about five days of good relief in the temporal parietal area, as well in the trigger point areas.

Side-Effects

The injection of this amount of bupivacaine in a conventional injectable form would have resulted in the onset of pain, inflammation and soreness at the injection site. Relief of pain would have been observed over our to eight hours before reoccurring.

Run B

This 43-year old lady is complaining of headaches; neck aches; pain in the mid-thoracic area; low back pain; pain going down the legs; pain going down the arms. She has had these for about ten years.

Ms. B started to have pains in her low back and neck with headaches following a motor vehicle accident in 1978. Following this she was involved in six other motor vehicle accidents. Over the years and with successive accidents, her symptoms increased until she had pains as noted above. Basically she is in pain all the time with pain throughout her body.

Physical examination has shown marked spasm of the whole of the paraspinal musculature from the nuchal line down to the sacrum. The sacroiliac joints were fixed. However, reflexes of the upper and lower limbs were normal indicating that there was no real radiculopathy.

Patient has Undergone the Following Investigations

1. X-rays of the cerival and lumbar spines showed some degenerative changes.
2. Her recent CT Myelograms of the lumbar and cervical spines did not reveal any disc herniations.
3. Facet diagnostic blocks of the lumbar and cerivcal spines were equivocal as to whether there was significant facet disease causing the pain or not.

Patient has Undergone the Following Unsuccessful Treatments

1. Analgesics and especially Fiorinal daily
2. Occasional muscle relaxants
3. Sedatives
4. She was turned down for a psychologically oriented rehabilitation program because it was felt that her problems were too severe and that she would not benefit.
5. Trigger point injections of the paraspinal muscles of the neck, thoracic spin and lumbar spine produced some temporary relief including some relief off the pain down the legs and arms.
6. Occipital blocks produced some temporary relief of the headaches.

The relief by local anesthetic blockades lasted one two days.

Treatment with the Inventive Formulation of Example 1

In the past month the patient was tried on long-acting bupivacaine. The injections were carried out into trigger point areas of the lumbar paravertebral musculature and glueteal musculature.

Result

The patient received about five days of good relief with these trigger point injections.

Side-Effects

With the long-acting Bupivacaine, it was again noted that there was less post-injection pain than the regular Bupivacaine. Furthermore there was no redness at the injection site. Furthermore, the post-injection irritability and general side-effects were less than is experienced with the use of regular Bupivacaine.

Run C

This 49-year old lady is complaining of constant neck ache; constant supraorbital pain; pain in the trapezii; mood, memory, concentration disturbances; uncontrolled weeping. She has had these since 1987.

Ms. C was well and active, working as an assistant school principal until 1987 when she was involved in a minor motor vehicle accident. Following this she developed the above-noted symptoms.

She has undergone fact diagnostic blocks which were positive and so indicated facet damage. She underwent facet joint rhizolysis which relieved the pain in her neck and supraorbital areas for about eight months, but then the pains returned. This was presumably to regeneration of the fact nerves.

She has been investigated by neuropsychologists because of her mood, memory and concentration and sleep disturbances. She appears to ahe a combination of minor head injury and post-traumatic emotional disorder. She has not been able to work for several years and this has contributed to a feeling of guilt and worthlessness.

The paracervical muscles are tender and swollen and the facet joints from C2 to C6 are tender bilaterally. The supraorbital nerves are tender to 3+.

Patient C has Undergone the Following Investigations

1. Facet diagnostic blocks which were positive
2. CT myelogram which showed a disc herniation at C5–6
3. CT scan of the brain which was normal
4. SPECT scan of the brain which was normal Patient C's Diagnosis is as Follows 1. Facet damage of the cervical spine causing the headaches including the frontal headaches
2. Cervical disc herniation
3. Post-traumatic emotional disorder
4. Possible minor head injury Patient C has Undergone the Following Unsuccessful Treatments 1. Antidepressants
2. Hypnotics for sleep 3. Analgesics for pain
4. Comprehensive psychotherapy
5. Occipital and supraorbital nerve blocks with trigger point injections of the paracervical muscles. These have produced about two days of relief after each block.

Treatment with the Inventive Preparation of Example 1

In the past month this patient was tried on long-acting Bupivacaine. The injections were carried out into the paracervical and trapezius musculature. As well as in the occipital nerves. In addition, supraorbital blocks were done.
Result The patient received about four to five days of good pain relief in the paracervical musculature, this cut down a lot of the occipital pain. In addition, the supraorbital blockade with long-acting Bupivacaine provided about 4 days of relief. In the past we had used regular Bupivacaine and this provided about 12 hours to one day of relief only.

Once again it was noted that there was no swelling or redness or sense of irritability such as post-injection pain with the present long-acting Bupivacaine formulations. The invention being thus described, it will be obvious that the same may be varied in many ways. Such variations are not be regarded as a departure from the spirit and scope of the invention and all such modifications are intended to be included within the scope of the following claims.

What is claimed is:

1. A sustained release delivery system, which comprises: an active therapeutic drug dispersed with a polymer matrix which is solubilized or suspended in a liquid medium; wherein the polymer matrix consists of hyaluronic acid of salts thereof blended with a nonionic polymer selected from the group consisting of hydroxyethylcellulose, hydroxypropylcellulose and mixture thereof; and wherein the molar ratio of the hyaluronic acid or salts thereof to the nonionic polymers 1:0.5 to 2.0.

2. The sustained release delivery systems of claim 1, wherein the hyaluronic acid salt is the sodium salt and has a sulphated ash content below about 15%, a protein content below about 5%, and is 95–100% free from contamination of related mucopolysaccharides.

3. The sustained release delivery system of claim 1, wherein the polymer matrix is an injectable solution.

4. The sustained release delivery system of claim 1, wherein the polymer matrix is a topical gel.

5. The sustained release delivery system of claim 1, wherein the nonionic polymer is hydroxyethyl cellulose.

6. A sustained release delivery system, which comprises: a polymer matrix suspended of solubilized in a liquid medium, wherein the polymer matrix contains mucopolysaccharides and derivatives thereof, blended with a nonionic polymer selected from the group consisting of hydroxyethylcellulose, hydroxypropylcellulose and mixtures thereof, and wherein the molar ratio of the negative charged polymer to the nonionic polymer is 1:0.5 to 2.

7. The sustained release release delivery systems of claim 6, wherein the muscopolysaccharide is hyaluronate acid of salts thereof and is selected from the group consisting of sodium, calcium, potassium or magnesium salt.

8. The sustained release delivery system of claim 6, wherein the nonionic polymer is selected from the group consisting of hydroxyethyl cellulose, hydroxypropyl cellulose and mixtures thereof.

9. The sustained release delivery system of claim 6, wherein the molar ratio of the polymers is 1:0.8 to 1.5.

10. The sustained release delivery system of claim 6, where the hyaluronic acid or salts thereof is present in amounts of about 0.1% to about 2.0% by weight.

11. The sustained release delivery system of claim 6, wherein the nonionic polymers are present in amounts of about 0.1% to about 1.0% by weight.

* * * * *

UNITED STATES PATENT AND TRADEMARK OFFICE
CERTIFICATE OF CORRECTION

PATENT NO. : 6,335,035 B1
DATED : January 1, 2002
INVENTOR(S) : Alan Drizen et al.

It is certified that error appears in the above-identified patent and that said Letters Patent is hereby corrected as shown below:

Column 11,
Line 33, change "of" to -- or -- (2nd occurrence)
Line 36, change "mixture" to -- mixtures --

Column 12,
Line 3, change "systems" to -- system --
Line 14, change "of" to -- or --
Line 20, change "systems" to -- system --
Line 21, change "of" to -- or --

Signed and Sealed this

Second Day of July, 2002

Attest:

Attesting Officer

JAMES E. ROGAN
Director of the United States Patent and Trademark Office